(12) United States Patent
Phillips (10) Patent No.: US 10,835,155 B2
(45) Date of Patent: Nov. 17, 2020

(54) ULTRA-CLEAN BAG OR BALLOON FOR COLLECTION OF VOLATILE ORGANIC COMPOUNDS IN BREATH OR AIR

(71) Applicant: Michael Phillips, Fort Lee, NJ (US)

(72) Inventor: Michael Phillips, Fort Lee, NJ (US)

(*) Notice: Subject to any disclaimer, the term of this patent is extended or adjusted under 35 U.S.C. 154(b) by 809 days.

(21) Appl. No.: 15/395,950

(22) Filed: Dec. 30, 2016

(65) Prior Publication Data
US 2017/0188887 A1 Jul. 6, 2017

Related U.S. Application Data

(60) Provisional application No. 62/273,328, filed on Dec. 30, 2015, provisional application No. 62/393,347, filed on Sep. 12, 2016.

(51) Int. Cl.
| | | |
|---|---|---|
| *A61B 5/097* | (2006.01) | |
| *A61B 10/00* | (2006.01) | |
| *A61B 5/08* | (2006.01) | |
| *G01N 1/22* | (2006.01) | |
| *G01N 33/497* | (2006.01) | |

(52) U.S. Cl.
CPC .............. *A61B 5/097* (2013.01); *A61B 5/082* (2013.01); *A61B 10/00* (2013.01); *G01N 1/2202* (2013.01); *A61B 2010/0087* (2013.01); *G01N 33/497* (2013.01); *G01N 2001/2244* (2013.01); *G01N 2033/4975* (2013.01)

(58) Field of Classification Search
CPC .. A61B 2010/0087; A61B 5/082; A61B 5/097
See application file for complete search history.

(56) References Cited

U.S. PATENT DOCUMENTS

| | | | |
|---|---|---|---|
| 2005/0177056 A1* | 8/2005 | Giron | A61B 5/097 600/543 |
| 2016/0242674 A1* | 8/2016 | Ahmad | A61B 5/082 |
| 2016/0331272 A1* | 11/2016 | Ahmad | A61B 5/082 |
| 2017/0074857 A1* | 3/2017 | Dennis | A61B 5/0836 |

OTHER PUBLICATIONS

Pauling, L., et al., Quantitative analysis of urine vapor and breath by gas-liquid partition chromatography. Proc Natl Acad Sci U S A, 1971. 68(10): p. 2374-2376 (abstract).
Phillips, M., et al., Volatile organic compounds in breath as markers of lung cancer: a cross-sectional study, The Lancet, vol. 353, No. 9168, p. 1930-1933, Jun. 5, 1999 (abstract).
(Continued)

*Primary Examiner* — Puya Agahi
(74) *Attorney, Agent, or Firm* — Porzio Bromberg & Newman P.C.

(57) ABSTRACT

A device and method is described for the collection of breath or air samples into a chemically clean bag or balloon, to facilitate analysis of volatile organic compounds (VOCs) in low concentrations in the collected samples. A reservoir of activated charcoal is introduced into the bag or balloon for initial removal of VOCs and it is then replaced with a similar reservoir of activated charcoal until the bag or balloon is employed to collect a sample. The device fulfills a long-felt need for collection of breath and air samples with a high VOC signal-to-noise ratio.

11 Claims, 14 Drawing Sheets

(56) References Cited

OTHER PUBLICATIONS

Phillips, M., et al., Prediction of lung cancer using volatile biomarkers in breath; Cancer Biomarkers, vol. 3, No. 2, pp. 95-109, 2007 (abstract).
Kostelc, M., et al., Analysis of lung air from patients with bronchogenic carcinoma and controls using gas chromatography-mass spectrometry, Journal of Chromatography B: Biomedical Sciences and Applications vol. 432, 1988, pp. 1-11 (abstract).
Bousamra et al., Quantitative analysis of exhaled carbonyl compounds distinguishes benign from malignant pulmonary disease, The Journal of Thoracic and Cardiovascular Surgery vol. 148, Issue 3, Sep. 2014, pp. 1074-1081 (abstract).
Gordon et al., Volatile organic compounds in exhaled air from patients with lung cancer, Clinical Chemistry, Aug. 1985, vol. 31 No. 8 1278-1282 (abstract).
Silkoff, The Aerocrine exhaled nitric oxide monitoring system NIOX is cleared by the US Food and Drug Administration for monitoring therapy in asthma; The Journal of Allergy and Clinical Immunology, Nov. 2004 vol. 114, Issue 5, pp. 1241-1256 (abstract).
Adiguzel et al., Breath sensors for lung cancer diagnosis, Biosensors and Bioelectronics vol. 65, Mar. 15, 2015, pp. 121-138 (abstract).
Peng et al., Detection of lung, breast, colorectal, and prostate cancers from exhaled breath using a single array of nanosensors, British Journal of Cancer (2010) 103, 542-551. doi:10.1038/sj.bjc.6605810 www.bjcancer.com Published online Jul. 20, 2010 (abstract).
Mozzoni et al., Plasma and EBC microRNAs as early biomarkers of non-small-cell lung cancer, Biomarkers pp. 679-686 | Received Sep. 6, 2013, Accepted Sep. 13, 2013, Published online: Oct. 8, 2013 (abstract).
Carpagnano et al., Med Oncol (2014) 31: 952. doi:10.1007/s12032-014-0952-1 (abstract).
Boedeker et al., Sniffer 5 dogs as part of a bimodal bionic research approach to develop a lung cancer screening, Interact CardioVasc Thorac Surg (2012) 14 (5): 511-515 (abstract).
Phillips et al., Detection of an Extended Human Volatome with Comprehensive Two-Dimensional Gas Chromatography Time-of-Flight Mass Spectrometry, • Sep. 25, 2013 http://dx.doi.org/10.1371/journal.pone.0075274 (abstract).
Phillips et al, Detection of volatile biomarkers of therapeutic radiation in breath, Published Jun. 24, 2013 • 2013 IOP Publishing Ltd Journal of Breath Research, vol. 7, No. 3 (abstract).
Miekisch et al., Data interpretation in breath biomarker research: pitfalls and directions, Published Aug. 2, 2012 • 2012 IOP Publishing Ltd Journal of Breath Research, vol. 6, No. 3 (abstract).
Van der Schee et al., Breathomics in Lung Disease, Chest. 2015;147(1):224-231. doi:10.1378/chest.14-0781 (abstract).
Centers for Disease Control & Prevention: Lung Cancer Statistics. http://wwwcdcgov/cancer/lung/statistics/.
Results of Initial Low-Dose Computed Tomographic Screening for Lung Cancer, N Engl J Med 2013; 368:1980-1991May 23, 2013DOI: 10.1056/NEJMoa1209120 (abstract).
Aberle et al, Results of the Two Incidence Screenings in the National Lung Screening Trial, N Engl J Med 2013; 369:920-931Sep. 5, 2013DOI: 10.1056/NEJMoa1208962 (abstract).
Jeffers et al., Effective Use of Low-Dose Computed Tomography Lung Cancer Screening, Current problems in Diagnostic Radiology. Sep.-Oct. 2013 vol. 42, Issue 5, pp. 220-230 (abstract).
Carlile, Lung cancer screening: where have we been? Where are we going?, The Journal of the Oklahoma State Medical Association [2015, 108(1):14-181] (abstract).
Sather et al., Promoting good clinical practices in the conduct of clinical trials: experiences in the department of veterans affairs cooperative studies program, Controlled Clinical Trials vol. 24, Issue 5, Oct. 2003, pp. 570-584 (abstract).
Phillips, Method for the Collection and Assay of Volatile Organic Compounds in Breath, Analytical Biochemistry vol. 247, Issue 2, May 1, 1997, pp. 272-278 (abstract).
Mente et al., The Use of the R Language for Medicinal Chemistry Applications, Current Topics in Medicinal Chemistry, vol. 12, No. 18, Sep. 2012, pp. 1957-1964(8) (abstract).
Gowda et al., Interactive XCMS Online: Simplifying Advanced Metabolomic Data Processing and Subsequent Statistical Analyses, Anal. Chem., 2014, 86 (14), pp. 6931-6939 (abstract).
Phillips et al., Breath biomarkers of active pulmonary tuberculosis, Tuberculosis vol. 90, Issue 2, Mar. 2010, pp. 145-151 (abstract).
Phillips et al., Detection of lung cancer using weighted digital analysis of breath biomarkers, Clinica Chimica Acta vol. 393, Issue 2, Jul. 17, 2008, pp. 76-84 (abstract).
Weinstein et al., Clinical Evaluation of Diagnostic Tests, American Journal of Roentgenology Diagnostic Imaging and Related Sciences, Jan. 2005, vol. 184 No. 1 (abstract).
Stein, Mass Spectral Reference Libraries: An Ever-Expanding Resource for Chemical Identification, Anal. Chem., 2012, 84 (17), pp. 7274-7282 DOI: 10.1021/ac301205z Publication Date (Web): Jun. 22, 2012 (abstract).
Handa et al., Exhaled Breath Analysis for Lung Cancer Detection Using Ion Mobility Spectrometry, • Published: Dec. 9, 2014; • http://dx.doi.org/10.1371/journal.pone.0114555 (abstract).
Westhoff et al., Ion mobility spectrometry for the detection of volatile organic compounds in exhaled breath of patients with lung cancer: results of a pilot study, Thorax 2009; 64 737-738 Published Online First: Aug. 28, 2009. doi: 10.1136/thx.2008.107409 (abstract).
Hakim et al., Volatile Organic Compounds of Lung Cancer and Possible Biochemical Pathways, University-Clinic for Anesthesia, Innsbruck Medical University, 6020 Innsbruck, Austria Chem. Rev., 2012, 112 (11), pp. 5949-5966 (abstract).
Filipiak et al., Comparative analyses of volatile organic compounds (VOCs) from patients, tumors and transformed cell lines for the validation of lung cancer-derived breath markers, Journal of Breath Research, vol. 8, No. 2 (abstract).

* cited by examiner

ULTRA-CLEAN BAG OR BALLOON FOR COLLECTION OF VOLATILE ORGANIC COMPOUNDS IN BREATH OR AIR

BACKGROUND OF THE INVENTION

The modern era of breath testing dawned in 1971, when Linus Pauling first reported that normal human breath contains large numbers of volatile organic compounds (VOCs) in low concentrations. The majority of these VOCs are exhaled in low parts per million (ppm) or parts per billion (ppb). Different analytical technologies have been employed to assay VOCs in breath, including 1-dimensional gas chromatography with mass spectrometry (GC MS) and electronic noses. Analysis of breath VOCs with comprehensive 2-dimensional gas chromatography and time-of-flight mass spectrometry (GC×GC TOF MS) has revealed a complex matrix of more than 2,000 different VOCs in individual samples of breath.

Breath collection is intrinsically safe, painless, and non-invasive, and breath VOC analysis has applications in diagnostic medicine because it provides clinically useful information. The composition of breath VOCs is altered in several diseases including lung cancer, breast cancer, and infections such as active pulmonary tuberculosis and influenza. Breath acetone is increased in diabetic ketoacidosis and breath nitric oxide is increased in bronchial asthma. Breath VOCs changes also occur in normal physiological processes such as exercise, oxidative stress, and pregnancy.

Breath VOC analysis holds great promise as a new tool for detection of diseases, but progress has been impeded by a major technical obstacle: the difficulty of collecting a sample that is suitable for analysis. Breath samples collected by inflation of a bag or balloon can be employed to assay VOCs that are exhaled in high concentrations e.g. ethanol. However, analysis of bag or balloon samples with sensitive detectors such as GC MS cannot detect most VOCs in breath because of their low signal-to-noise ratio. The high background noise of VOCs in bags or balloons usually overwhelms the detector, and drowns out the signals generated by the breath VOCs.

The background noise in bags and balloons arises from volatile chemical contaminants (e.g. adhesives and plasticizers) that are introduced during manufacture. Even gas collection bags that are constructed from low-emission materials (e.g. Tedlar, Nylon) are generally contaminated by background VOC noise that may exceed the breath VOC signal by two or more orders of magnitude. This background noise persists even after a bag has been flushed several times with clean gases because the walls of the bag continue to outgas residual contaminants for long periods of time.

As a consequence, researchers have developed instruments for breath VOC collection that do not employ bags and balloons. These instruments are generally complicated and expensive, and require a trained operator to collect a sample. Other devices have been developed for the collection of breath into bags and balloon, but none have employed methods for making them chemically clean prior to use.

It is desirable to provide an improved apparatus and method to collect breath sample having a high signal-to noise ratio and at low cost.

SUMMARY OF THE INVENTION

The present invention relates to an improved apparatus and method to collect breath samples. The present invention has the advantages of:

1. A high signal-to-noise ratio that enables the assay of breath and air VOCs in low concentrations (ppm or ppb).
2. Low cost
3. Convenience and simplicity of operation, so that technically satisfactory samples can be collected by operators without special training.

An apparatus and method for collecting breath samples includes a housing. The housing can be an inflatable bag or balloon constructed from a low-emission material, such as biaxially-oriented polyethylene terephthalate. For example, the housing can be formed of a metallized Mylar. Activated charcoal is associated with the housing for removing background VOC contamination. A breath sample is collected in the housing after the removal of background VOC contamination.

In one embodiment, the present invention provides a method of sustaining the low level of background VOC contamination using indwelling activated charcoal prior to collection of a breath sample. In one embodiment, the present invention provides a method of collecting a breath sample that can be employed for assay of VOCs in low concentrations. In one embodiment, the present invention provides a method for collecting an air sample that can be employed for assay of VOCs in low concentrations.

In one embodiment, an initial cleaning uses a first strip of activated charcoal inserted into a neck of the housing. The first strip is removed and a second strip is inserted into the neck of the housing. The second cleaning procedure ensures that the housing is chemically cleaned of VOCs down to parts per billion prior to use. In this embodiment, two separate cleaning processes are used, both with a strip of activated carbon impregnated paper. The first cleaning can occur in a lab or production facility before the housing is sent to a user. The first strip of activated charcoal is then removed and replaced with a second strip of activated charcoal. The housing is folded such that the second strip is not exposed to most of housing. The folded housing can be placed in a container such as an envelope and forwarded to a user. A second cleaning is performed by the user who unfolds the housing. This exposes the second strip to the entire interior surface of the housing for a second cleaning. For example, the second cleaning can be performed overnight, prior to use.

The invention will be more fully described by reference to the following drawings.

DETAILED DESCRIPTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 1:
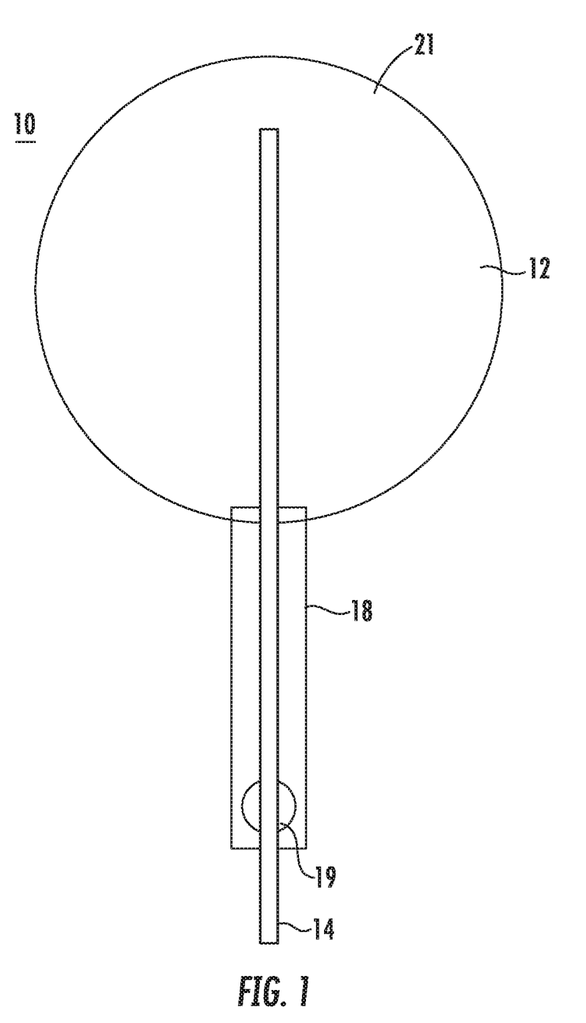
FIG. 1 is a schematic diagram of breath collection device before use.

FIG. 1 is a schematic diagram for an apparatus for collection of breath 10 in accordance with the teachings of the present invention. Housing 12 is inflatable with breath. In one embodiment, housing 12 is an inflatable bag or balloon. Preferably, housing 12 is a low-emission metallized Mylar inflatable balloon with a volume of about 1.0 to about 1.5 l when inflated. It will be appreciated that other sizes or configurations of housing 12 can be used in accordance with the teachings of the present invention.

Contaminant removal material 14 is associated with in housing 12. In one embodiment contaminant removal material 14 is a reservoir of activated carbon. This reservoir may take different forms, including a strip of activated-carbon paper, or a perforated tube filled with granules of activated charcoal. Containment removal material 14 is inserted through opening 19 of neck 18 into interior 21 of housing 12. Contaminant VOCs in the bag diffuse into the ultra-clean helium and are then captured on the activated charcoal by sorbent trapping. Serial analysis of the VOCs in the helium with GC MS have shown that overnight cleaning of the bag with this method removes approximately 99.9% of all VOCs that were initially detectable.

In a method of sustaining low background VOC contamination prior to collection of breath sample, following the initial removal of contaminant VOCs described above, a new reservoir of activated charcoal is inserted into the bag in the same fashion, and kept in place until the bag is used for a breath sample collection. The neck of the bag is temporarily sealed in order to prevent entry of ambient air VOCs into housing 12.

Figure 2:
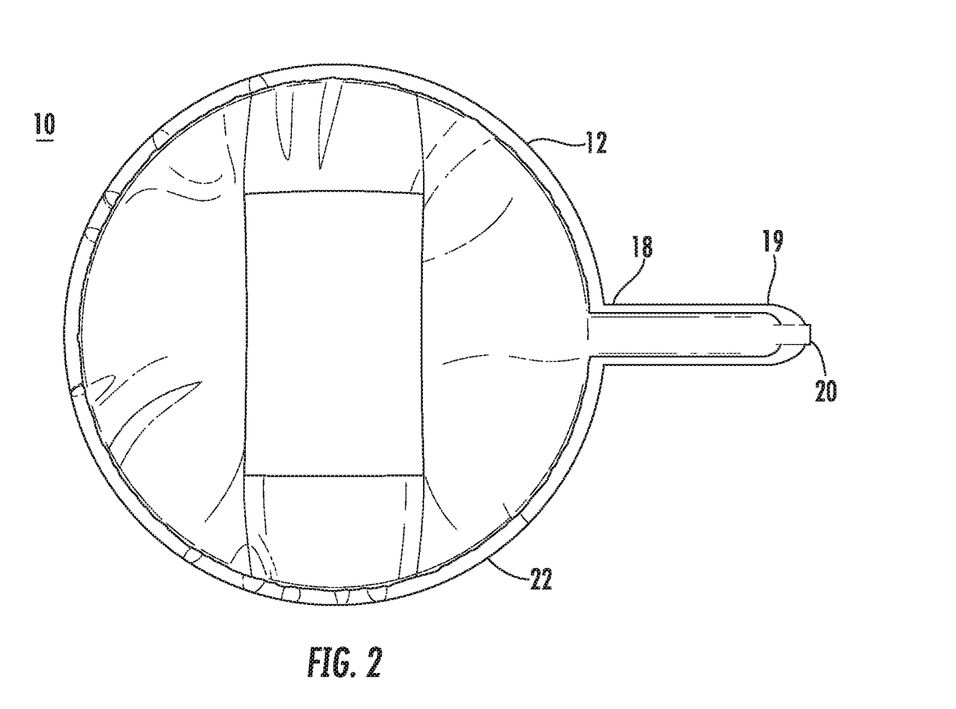
FIG. 2 is a schematic diagram of breath collection device before use.

In a method of removing background VOC contamination as shown in FIGS. 2-5. A reservoir of activated charcoal is introduced into housing 12 through its neck as shown in FIG. 2. This reservoir may take different forms, including a strip of activated-carbon paper, or a perforated tube filled with granules of activated charcoal. Closure 20 can be used for closing housing 12 before use. Closure 20 can be a spring-loaded clip. Label 22 can be affixed to housing 12. Housing 12 is gently inflated with ultra-clean helium in a quantity sufficient to separate the walls of housing 12. Conduit 16 can be inserted into neck 18 of housing 12 through opening 19.

In the method for collecting a breath sample:

1. Closure 20 as shown in FIG. 2 is removed, and the reservoir of activated charcoal is withdrawn from housing 12.

2. Residual helium is removed by manually stroking housing 12.

Figure 3:
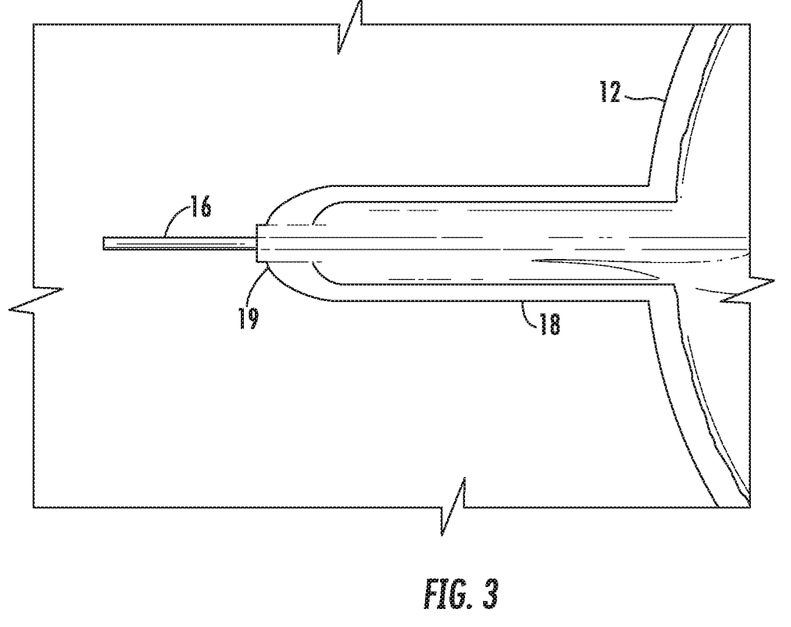
FIG. 3 is a schematic diagram of a conduit used with the breath collection device.

3. Conduit 16, such as a drinking straw, is inserted into the bag through its neck 18 as shown in FIG. 3.

Figure 4:
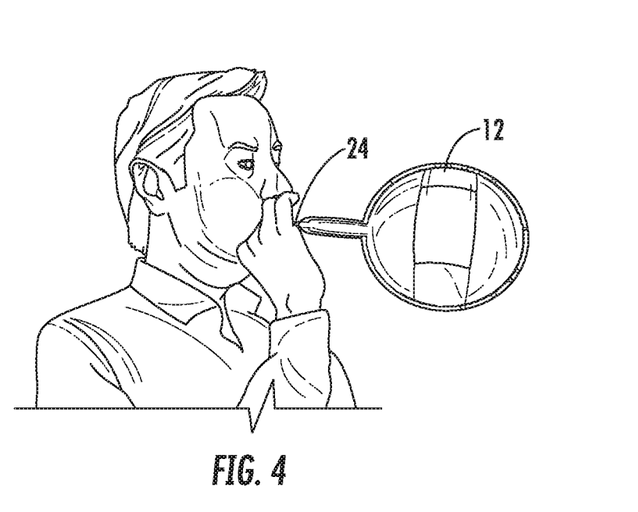
FIG. 4 is a schematic diagram of breath collection device during use.

4. The subject inflates the housing 12 with breath as shown in FIG. 4.

Figure 5:
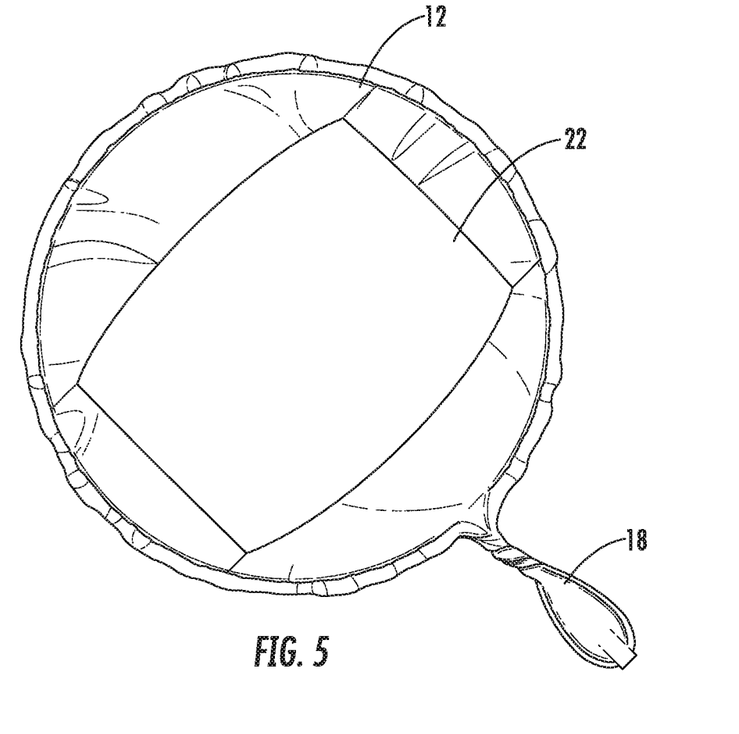
FIG. 5 is a schematic diagram of the breath collection device after use.

5. The conduit 16 is removed, and a tight knot is tied in the neck 18 of the housing 12 to prevent loss of the breath sample as shown in FIG. 5.

6. When required, a sample of breath is withdrawn from the bag for assay with a standard analytic method e.g. GC MS.

Figure 6:
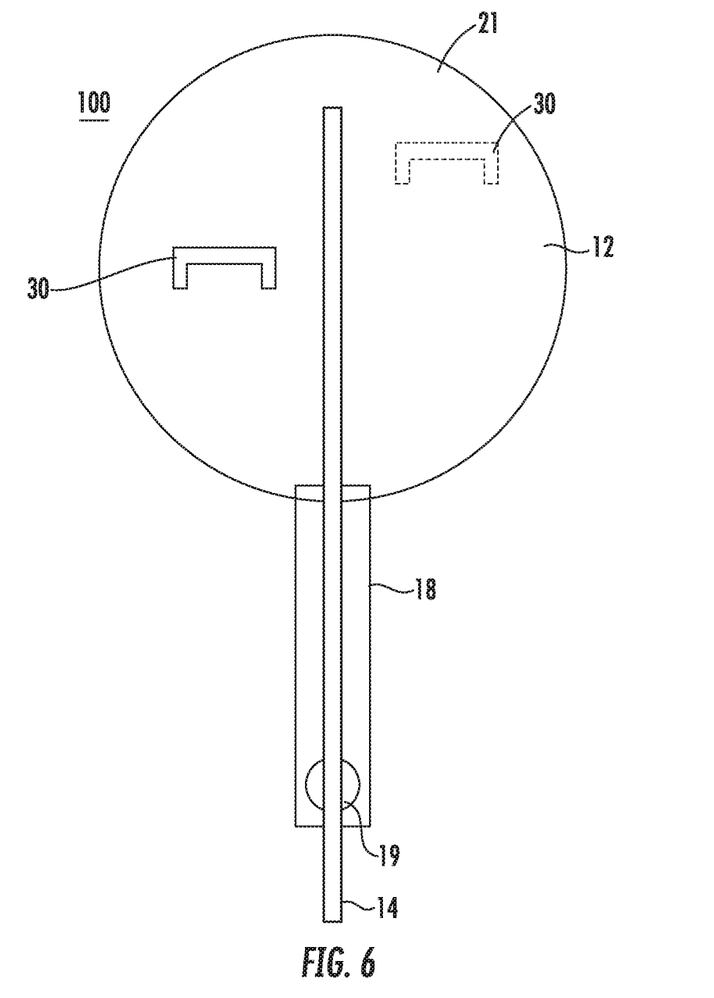
FIG. 6 is a schematic diagram of an ambient air collection device.

In a method for collecting an air sample: Ambient air may collected for assay in an analogous fashion with ambient air collection device 100 as shown in FIG. 6. In this ambient Handles 30 are affixed to housing 12, such as with adhesive to the opposite walls of the bag. In the method for collecting ambient air:

1. Closure 20 is removed, and the reservoir of activated charcoal is withdrawn from housing 12.

2. Residual helium is removed by manually stroking housing 12.

3. Housing 12 is inflated with ambient air by drawing the two handles apart from one another.

4. A tight knot is tied in the neck of 18 housing 20 to prevent loss of the air sample.

5. When required, a sample of air is withdrawn from the bag for assay with a standard analytic method e.g. GC MS.

FIGS. 7-13 illustrate a method of initial cleaning, removing background VOC contamination and collecting a sample.

Figure 7:
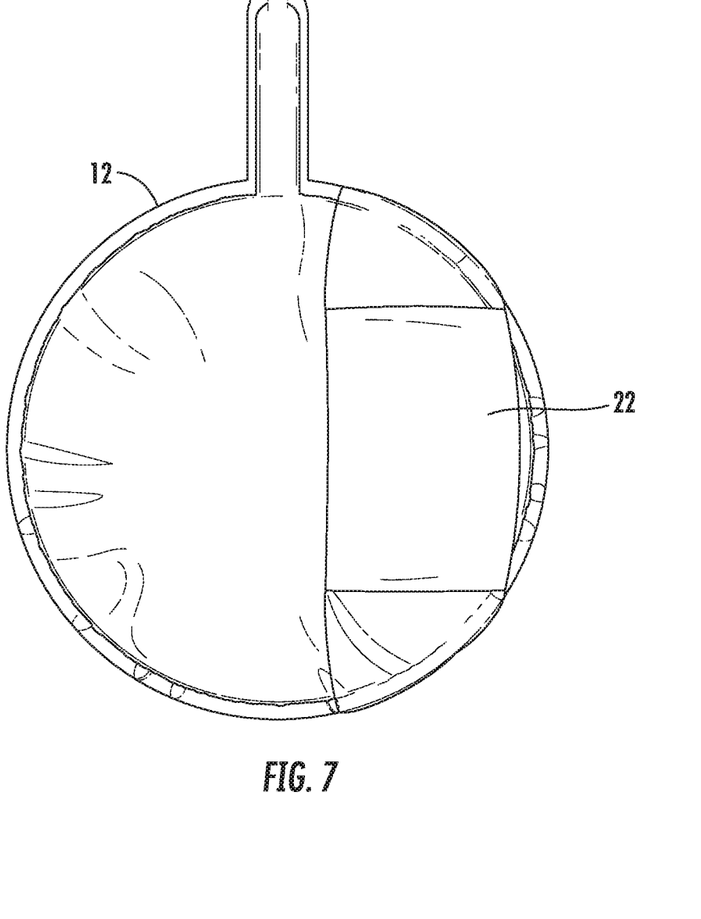
FIG. 7 is a schematic diagram of breath collection device before use.

In the method:

1. Housing 12 is labeled with label 22 which can be affixed to housing 12 as shown in FIG. 7.

Figure 8A:
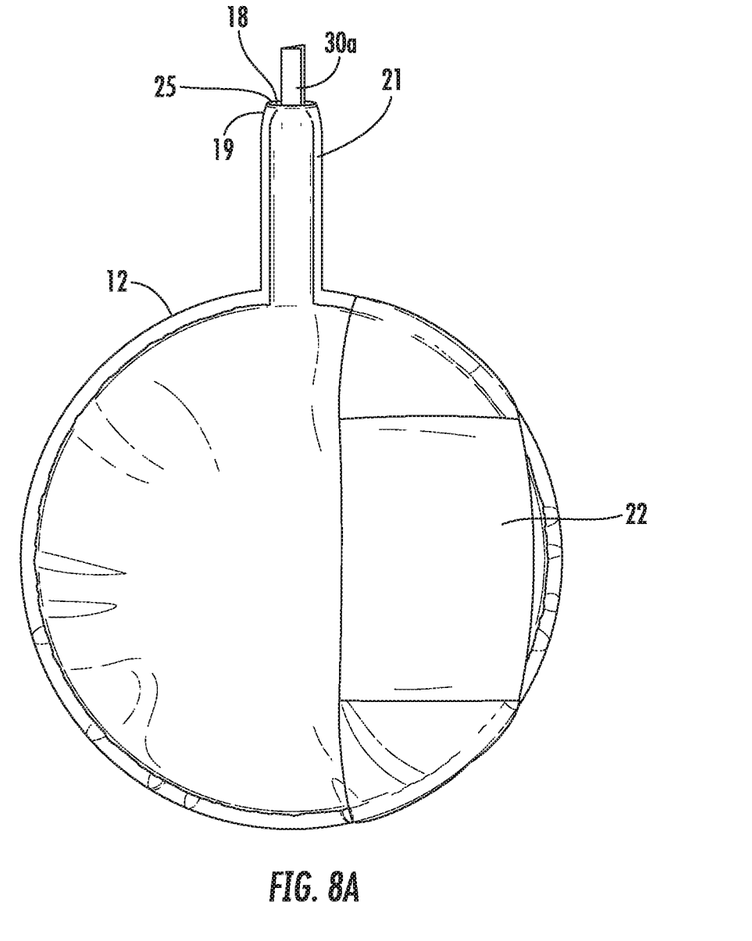
FIG. 8A is a schematic diagram of breath collection device before use.

2. A first reservoir of activated charcoal 30a is introduced into housing 12 through opening 19 in neck 18 as shown in FIG. 8A. This reservoir may take different forms, including a strip of activated-carbon paper. For example, the strip of activated carbon paper can be a 1 inch by 12 inch strip of Onyx Cellulose paper. The strip of activated carbon paper can be heated in an oven that is debris free and does not contain VOC emitting materials. For example, the activated carbon paper can be heated for 15 minutes at 150 degrees C. The activated carbon paper can be removed from the oven and cooled. The activated carbon paper can be folded and insert into neck 18 leaving end portion 25 extending from neck 18. For example, end portion 25 can be about 1.0 to about 1.5 cm.

Figure 10:
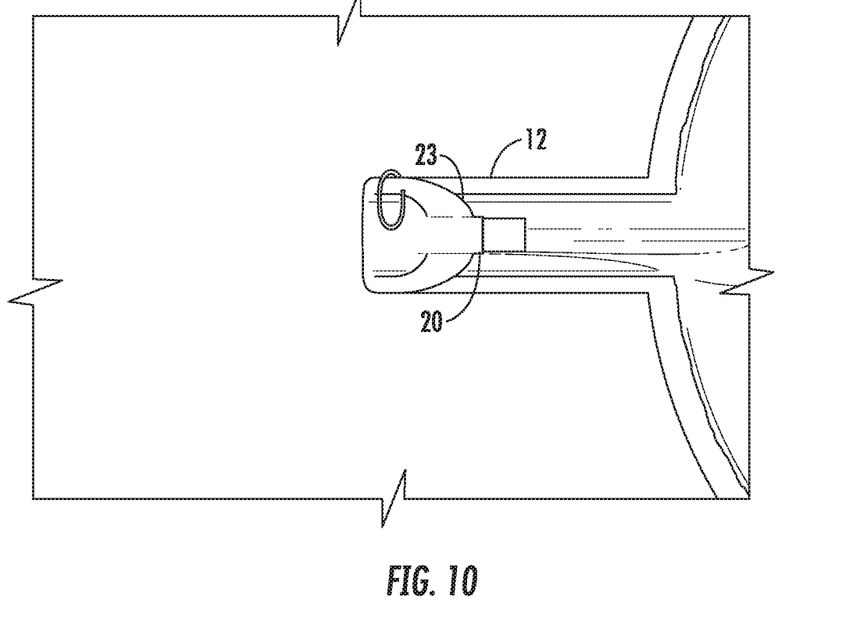
FIG. 10 is a schematic diagram of breath collection device before use.

3. During initial cleaning of housing 12, a small amount of purified Helium is filled through opening 19 in neck 18 to allow inner surfaces of housing 12 to be separated from one another. End 23 of housing 12 can be folded and secured with closure 20 as shown in FIG. 10 to ensure Helium does not escape housing 12. Housing 12 can sit at room temperature for at least one day. In one embodiment, before folding housing 12, conduit 16, such as a drinking straw, can be inserted into housing 12 through opening 19 in neck 18 for example as shown in FIG. 3.

Figure 8B:
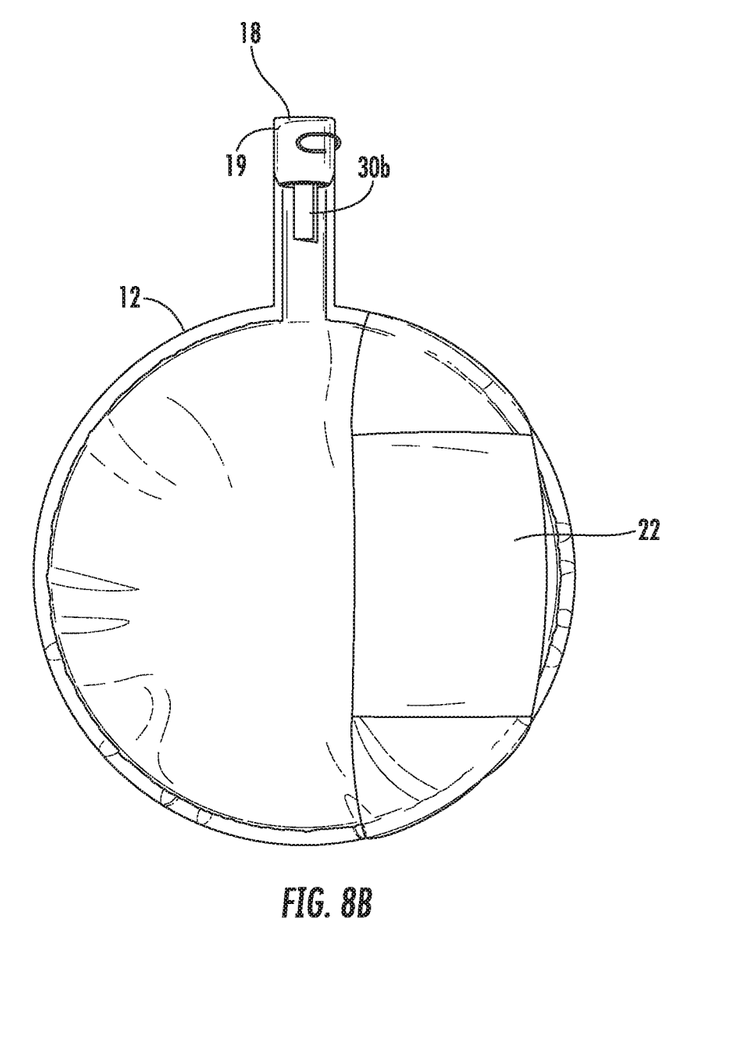
FIG. 8B is a schematic diagram of the breath collection device including a reservoir of activated carbon.
Figure 9A:
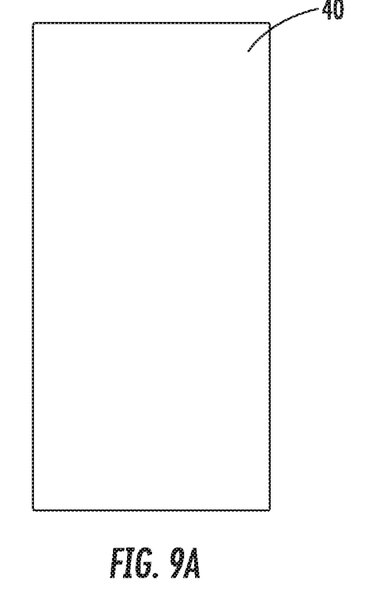
FIGS. 9A-9D are schematic diagrams of packaging which can be used with the breath collection device.
Figure 9B:
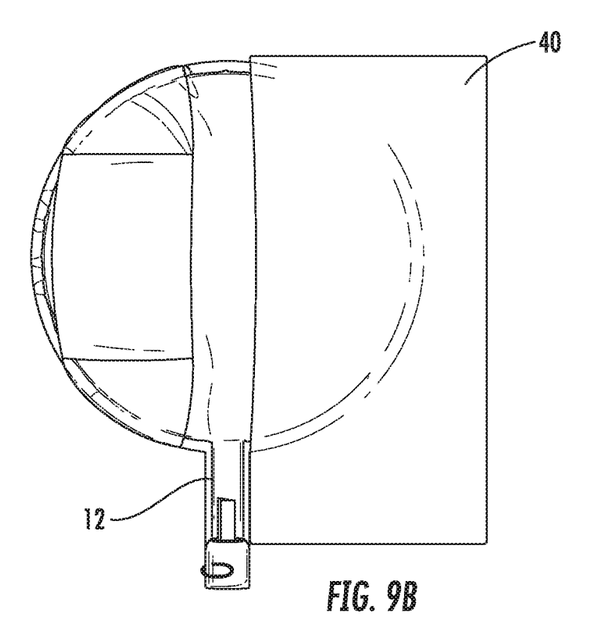
Figure 9C:
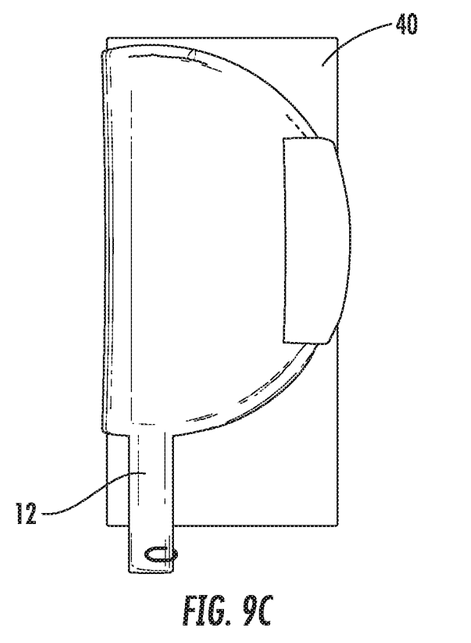
Figure 9D:
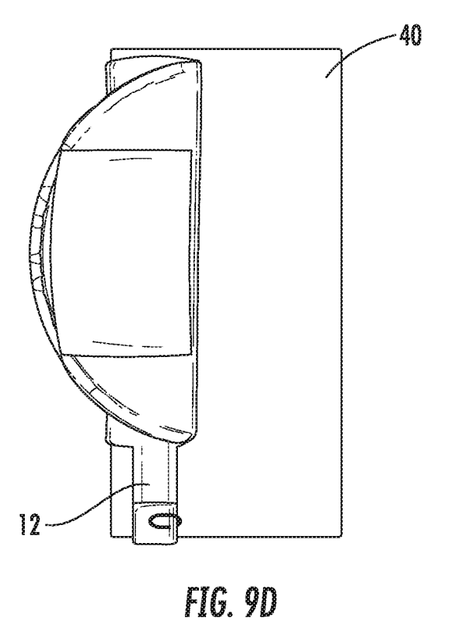

4. After initial cleaning, referring to FIG. 8A, reservoir of activated charcoal 30a is removed from housing 12. Housing 12 can be pressed together to release Helium from housing 12. A second reservoir of activated charcoal 30b, inserted through opening 19 in neck 18 as shown in FIG. 8B. Neck 18 can include a pocket for receiving reservoir of activated charcoal 30b. End 23 of housing 12 can be folded and secured with closure 20 to prevent reservoir of activated charcoal 30b from being exposed to the inner portion of housing 12. Housing 12 can be sealed and placed in inner envelope 40 as shown in FIGS. 9A-D.

5. On the day before use, housing 12 can be removed from inner envelope 40 as shown in FIG. 10. Housing 12 can be unfolded with closure 20 remaining in place and left for a period of time, for example overnight.

Figure 11:
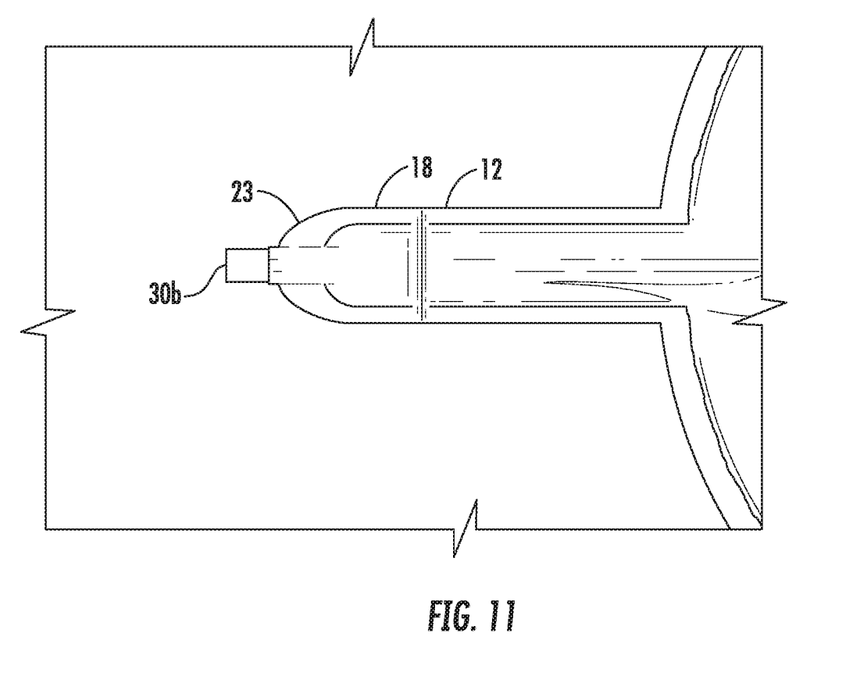
FIG. 11 is a schematic diagram of breath collection device before use.

6. On the day of use, closure 20 is removed from housing 12 as shown in FIG. 11. Neck 18 is unfolded. Second reservoir of activated charcoal 30b is removed from housing 12 and discarded.

Figure 12:
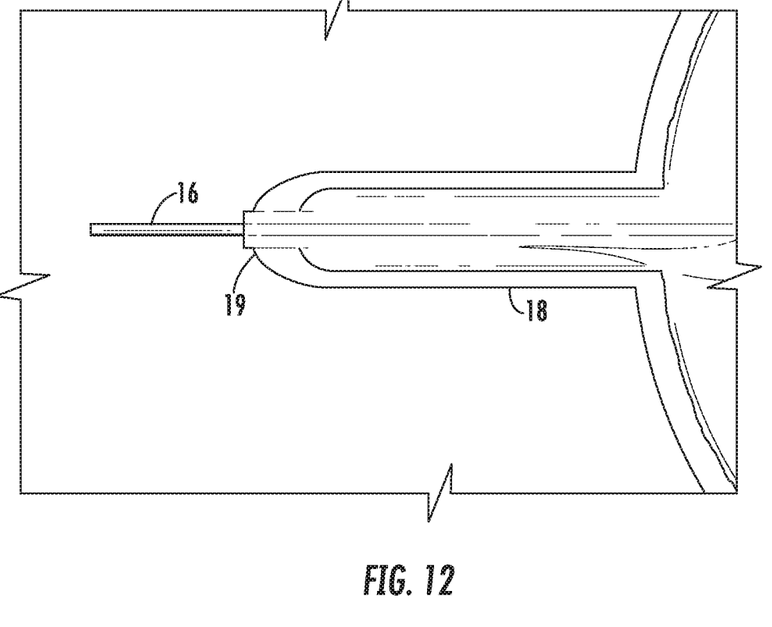
FIG. 12 is a schematic diagram of breath collection device prepared for use.

7. If conduit 16 is not present in housing 12, conduit 16 is inserted into opening 19 in neck 18 of housing 12 as shown in FIG. 12.

8. Housing 12 is inflated with breath from a subject through conduit 16.

9. Conduit 16 is removed and a tight knot is tied in neck of 18 housing 12 to prevent loss of the air sample.

Figure 13A:
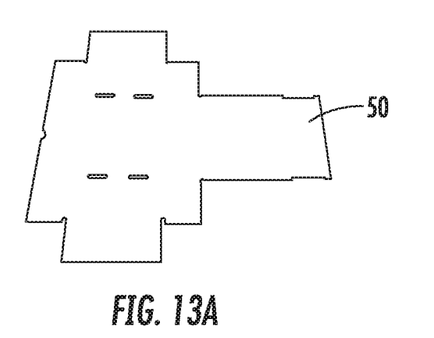
FIG. 13A-13C are schematic diagrams of a box which can be used with the breath collection device.
Figure 13B:
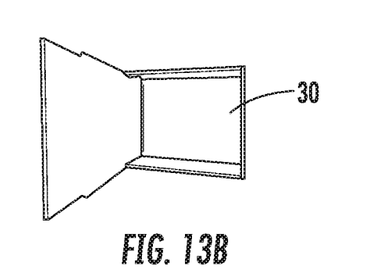
Figure 13C:
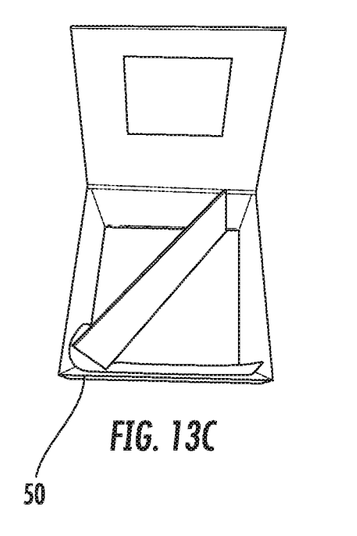

10. Housing 12 is placed in box 50. For example, box 50 can be prepared as shown in FIGS. 13A-13C.

Figure 14A:
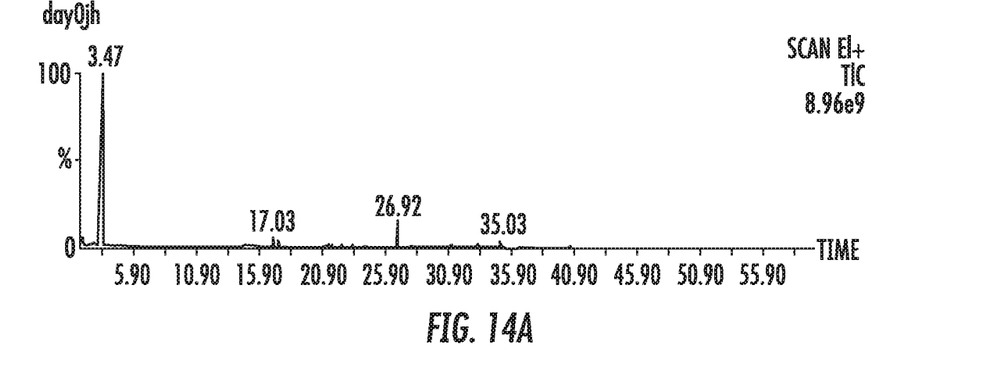
FIGS. 14A-14C are diagrams of a chromatograph after use of the breath collection device.
Figure 14B:
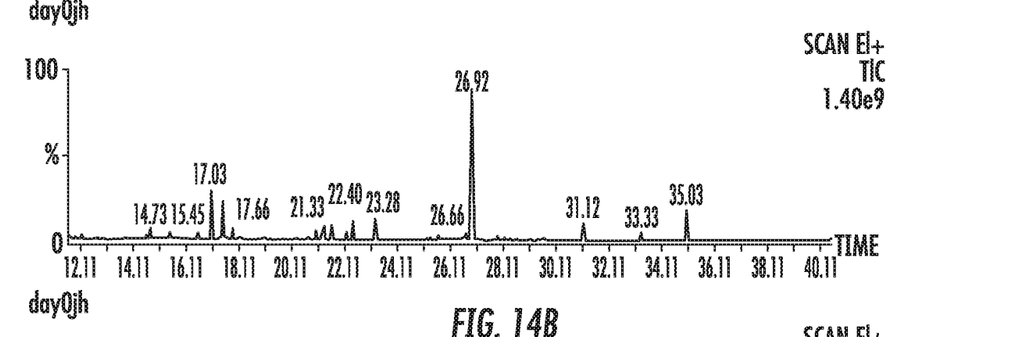
Figure 14C:
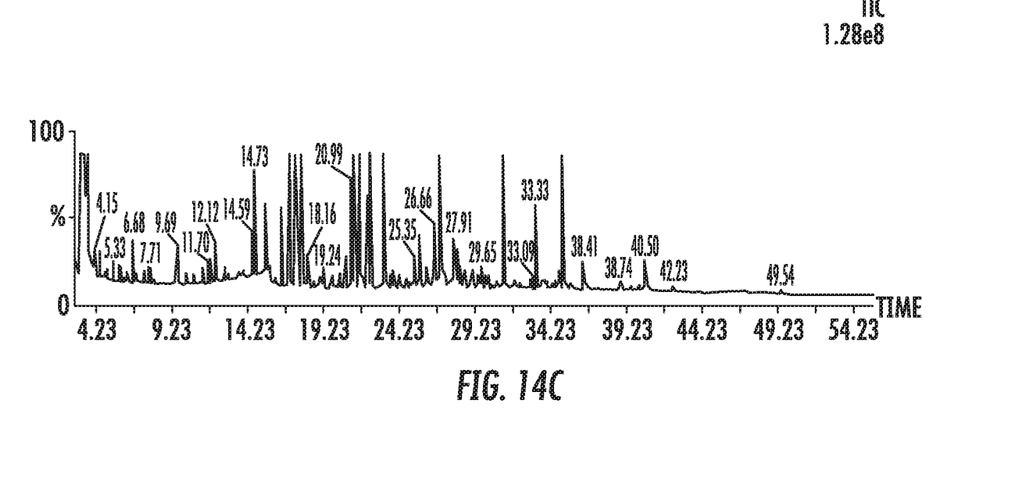

FIG. 14 A-C relate to is a chromatograma of a breath VOC sample collected with an apparatus for collecting breath 10 and then analyzed with GC SAW (gas chromatography surface acoustic wave detection) in which the x-axis=time, y-axis=instrument response. FIG. 14A is an image of an entire chromatogram. The first peaks, acetone and isoprene, are present in great abundance relative to the other peaks which causes the presence of the other peaks to be difficult to discern. FIG. 14 B is an image of a chromatogram which expands the x axis scale to demonstrate that there are many small peaks with one large peak eluting at 26.92 min. FIG. 14 C is an image of a chromatogram which expands the x axis and truncates the peaks in the y axis in order to demonstrate that there are many small peaks present. It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. An apparatus for collecting a breath sample comprising;
   a housing, the housing is a foldable inflatable bag or balloon, the housing having a neck; and
   a first contaminant removal reservoir, the first contaminant removal reservoir is formed of activated charcoal;
   wherein the first contaminant removal reservoir is inserted into the neck of the housing, a first portion of the contaminant removal reservoir extending into an interior of the housing to capture volatile organic compounds by sorbent trapping on the first contaminant removal reservoir to remove volatile organic compounds from within the interior of the housing when the first contaminant removal reservoir is removed from the housing, a second portion of the contaminant removal reservoir extending from the neck to remove the first contaminant removal reservoir, the first contaminant removal reservoir being removed before collecting the breath sample within the interior of the housing.

2. The apparatus for collecting a breath sample of claim 1 wherein the housing is formed of a biaxially-oriented polyethylene terephthalate.

3. The apparatus for collecting a breath sample of claim 1 wherein the housing is formed of a metallized Mylar.

4. The apparatus for collecting a breath sample of claim 1 wherein the first contaminant removal reservoir is formed of an impregnated paper strip of the activated charcoal.

5. The apparatus for collecting a breath sample of claim 1 wherein the first contaminant removal reservoir is a perforated tube filled with granules of the activated charcoal.

6. The apparatus for collecting a breath sample of claim 1 wherein after the first cleaning reservoir is removed from the neck of the housing a second contaminant removal is inserted into the neck of the housing before collecting the breath sample, the housing being folded after insertion of the second contaminant removal reservoir such that the second contaminant removal reservoir is not exposed the interior of the housing and the housing being unfolded to expose the second contaminant removal reservoir to the interior of the hosing for a second cleaning.

7. The apparatus for collecting a breath sample of claim 1 further comprising a conduit, the conduit being inserted into the neck of the housing after removal of the first contaminant removal reservoir.

8. The apparatus for collecting a breath sample of claim 1 further comprising a closure for closing the housing before use.

9. The apparatus of claim 6 wherein the second contaminant removal reservoir is formed of activated charcoal impregnated paper.

10. The apparatus for collecting a breath sample of claim 6 wherein the second contaminant removal reservoir is a perforated tube filled with granules of activated charcoal.

11. The apparatus for collecting a breath sample of claim 6 wherein the closure is a spring loaded clip.

* * * * *